United States Patent [19]

Komiya

[11] 4,240,431
[45] Dec. 23, 1980

[54] LASER KNIFE

[75] Inventor: Osamu Komiya, Hachioji, Japan

[73] Assignee: Olympus Optical Co., Ltd., Tokyo, Japan

[21] Appl. No.: 902,841

[22] Filed: May 4, 1978

[30] Foreign Application Priority Data

| May 16, 1977 | [JP] | Japan | 52-56635 |
| May 16, 1977 | [JP] | Japan | 52-62824[U] |
| Jun. 24, 1977 | [JP] | Japan | 52-83289[U] |

[51] Int. Cl.³ .................. A61B 17/36; H23K 9/00
[52] U.S. Cl. .................. 128/303.1; 219/121 LG; 219/121 LB
[58] Field of Search ........................ 128/4-8, 128/303.1, 395, 305, 634; 350/96.26; 219/121 L, 121 LM, 121 LG, 121 LB, 121 LN

[56] References Cited

U.S. PATENT DOCUMENTS

| 3,123,066 | 3/1964 | Brumley | 128/397 |
| 3,417,746 | 12/1968 | Moore et al. | 128/6 |
| 3,599,630 | 8/1971 | Sato | 350/96.26 |
| 3,700,850 | 10/1972 | Lumley et al. | 219/121 LM |
| 3,858,577 | 1/1975 | Bass et al. | 128/8 |
| 3,865,113 | 2/1975 | Sharon et al. | 128/303.1 |
| 4,087,672 | 5/1978 | Yi | 219/121 LM |
| 4,126,136 | 11/1978 | Auth et al. | 128/305 |
| 4,146,019 | 3/1979 | Bass et al. | 128/6 |

OTHER PUBLICATIONS

Wolbarsht, Laser Applications in Medicine and Biology, vol. 2, ©1974, Plenum Press, New York, pp. 257, 258 & 304, 305.
Gagliano et al., Laser Beam Welder; Western Electric Tech. Digest #36 Oct. 1974, pp. 11, 12.
Blessinger, Jr.; Pierce Control for Laserbeam & Drilling Through Glass; RCA Tech. Notes #TN1160, 7/76, 2 sheets.
Meyer et al., A Laser Stimulator for the Study of Cutaneous Thermal & Pain Sensation; IEEE Trans. on Bio. Med. Engineering; vol. BME-23; #1, pp. 54-60, 1/76.

*Primary Examiner*—Robert W. Michell
*Assistant Examiner*—Arthur S. Rose
*Attorney, Agent, or Firm*—Weinstein & Sutton

[57] ABSTRACT

A laser knife includes a tubular member adapted to be inserted into the coeloma by being inserted into the forceps channel of an endoscope, a pair of oppositely located laser radiation emitter and acceptor members on the distal end of the tubular member, a laser radiation receiving element disposed on the acceptor for accepting laser radiation which is used for purpose of cautery subsequent to the completion thereof and performing a photoelectric conversion of such radiation, a laser radiation transmission member for transmitting laser radiation to the emitter, and a laser radiation isolator interposed between the transmission member and a laser oscillator and responsive to a laser radiation accept signal from the element for interrupting the supply of laser radiation into the transmission member. In this manner, unwanted irradiation of normal tissues with the laser radiation is automatically terminated after a desired affected part has been cauterized.

18 Claims, 17 Drawing Figures

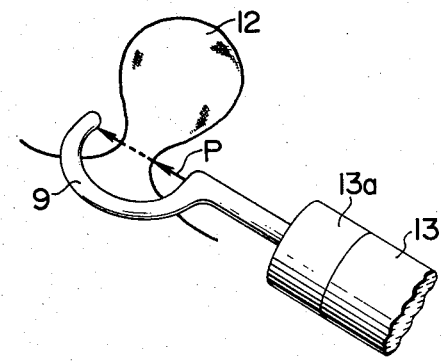
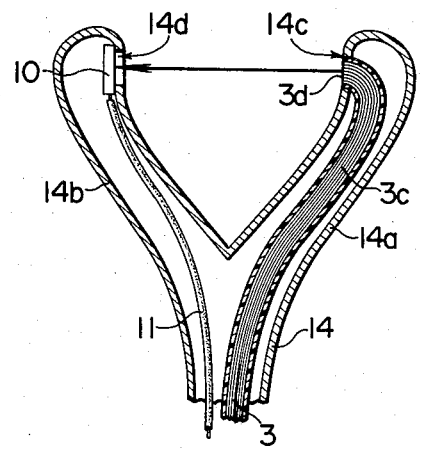
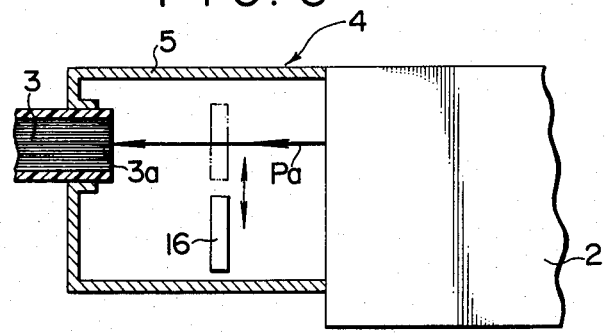
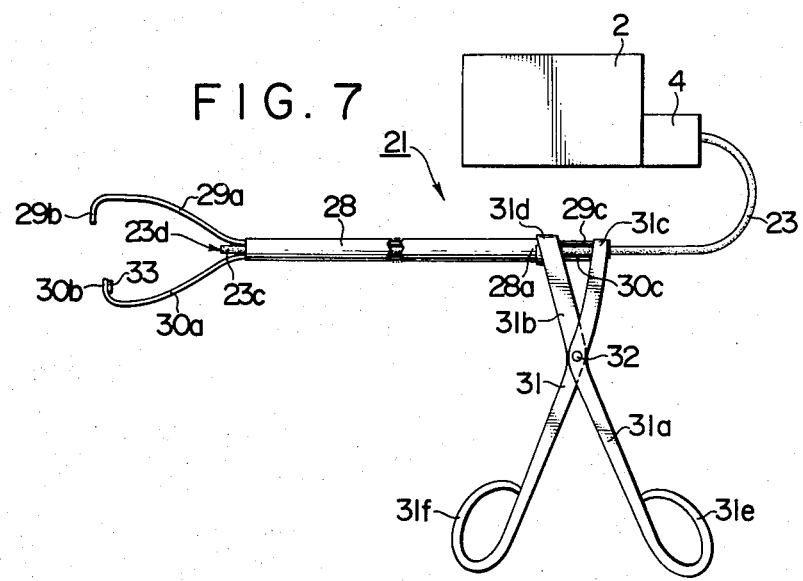

LASER KNIFE

BACKGROUND OF THE INVENTION

The invention relates to a laser knife, and more particularly to a laser knife of the type which is used to cauterize the tissues of an affected part located within the coeloma with laser radiation for purpose of excision or coagulation.

The conventional practice in the incision or excision of an affected part such as a polyp located within the coeloma has been by the use of excision or incision knife which is inserted into the forceps channel formed by a flexible tube of an endoscope and which is moved into or out of the distal end of the tube. However, the use of such excision or incision means requires a high level of skill and is also time consuming. In addition, treatments such as stanching or sterilization must be performed, resulting in a tremendous operation. An attempt has been made to avoid such disadvantages by using laser radiation which is directed toward an affected part to irradiate and cauterize it for purpose of excision or incision. While such a technique is advantageous in that the necessity of stanching or sterilization is avoided, the very high intensity of laser radiation employed involves the risk that unintended parts of the physical body may be irradiated after the radiation has been effectively utilized to cauterize the intended part, thus causing undesirable cautery or piercing of normal tissues. Nevertheless, it is appreciated that the surgical operation such as excision or incision could be simply completed within a very reduced length of time if provision is made to avoid an unintended irradiation with laser radiation.

SUMMARY OF THE INVENTION

It is an object of the invention to avoid the disadvantages of the prior art by providing a laser knife which irradiates an affected part with laser radiation and which interrupts the irradiation automatically whenever the intended part has been cauterized for purpose of incision or excision.

It is another object of the invention to provide a laser knife which irradiates an intended affected part with laser radiation while firmly holding such part and which automatically interrupts the irradiation immediately after the completion of cautery of the intended part.

With the laser knife of the invention, the cautery and hence the incision or excision of an affected part can be completed within a significantly reduced length of time by irradiating the intended part with laser radiation while viewing it with an endoscope. No particular skill is required for its operation, which can be simply achieved. As soon as the affected part is incised or excised, the irradiation with laser radiation is automatically interrupted, preventing any risk that other normal tissues may be cauterized. In this manner, the safety of operation is assured. The cautery by means of laser radiation avoids the need for stanching or sterilization. During the irradiation, the intended part is firmly held, and hence laser radiation can be positively directed to the intended area. The intensity of laser radiation can be adjusted to extend the applicability of the laser knife of the invention. When the intensity is reduced, it may be used for cautery of a salpinx for purpose of contraception.

BRIEF DESCRIPTION OF THE DRAWINGS

FIG. 4 is a perspective view of the laser knife illustrating its use in the excision of a polyp located within the coeloma;

FIG. 5 is an enlarged cross section of a laser knife according to another embodiment of the invention;

FIG. 6 is an enlarged cross section of another form of laser radiation isolation unit;

FIG. 7 is a side elevation of a laser knife according to a further embodiment of the invention;

DESCRIPTION OF PREFERRED EMBODIMENTS

Figure 1:
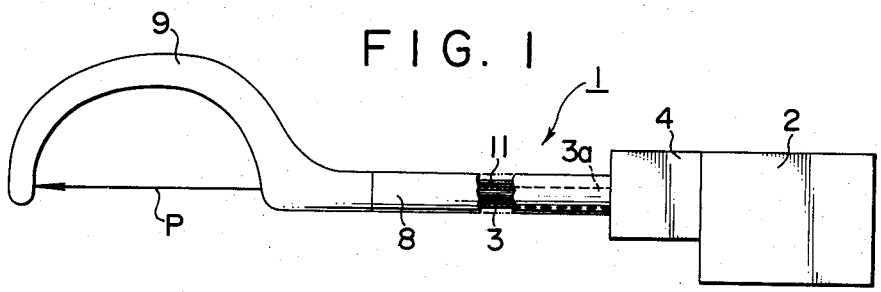
FIG. 1 is a side elevation of a laser knife according to one embodiment of the invention.

Referring to FIG. 1, there is shown a side elevation of a laser knife 1 constructed in accordance with one embodiment of the invention. Laser radiation from a laser oscillator 2 is introduced into a laser radiation transmission member 3 through a laser radiation isolation unit 4.

Figure 3:
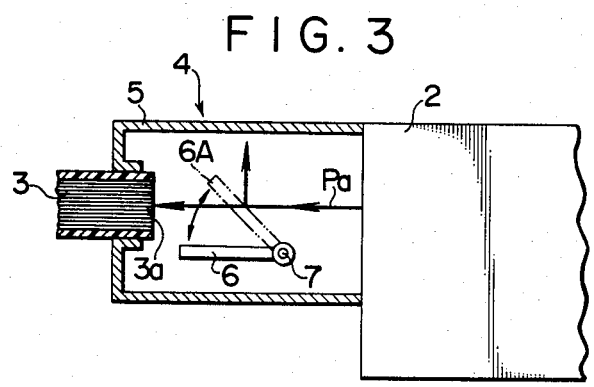
FIG. 3 is a fragmentary cross section, to an enlarged scale, of the laser radiation isolation unit shown in FIG. 1.

One form of laser radiation isolation unit 4 is shown in FIG. 3. Referring to this Figure, it includes a housing 5 which is located next to the oscillator 2 and detachably receiving one end 3a of the transmission member 3. The unit 4 also includes an isolation member 6 disposed within the housing and movable into and out of a path Pa along which laser radiation P from the oscillator 2 is directed to the end 3a of the transmission member 3, and electromagnetic means, not shown, which responds to a signal from laser radiation receiving element 10 to be described later for controlling the movement of the isolation member 6. The isolation member 6 is formed as a reflecting mirror, and has its one end pivotally mounted on a pin 7. Normally it remains stationary at a position which is retracted from the path Pa. However, when the electromagnetic means, not shown, responsive to a signal from the element 10 is activated, the member 6 is driven by this means to move angularly about the pin 7 into the path Pa, or to the phantom line position 6A, thus interrupting the transmission of laser radiation into the transmission member 3.

Figure 2:
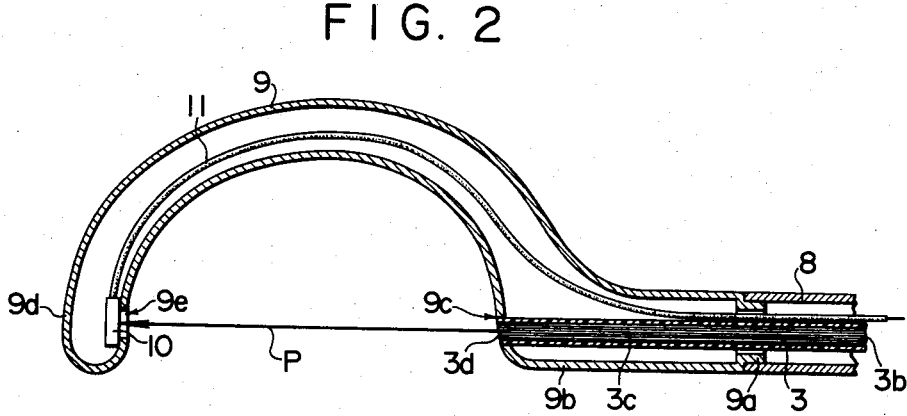
FIG. 2 is a fragmentary cross section, to an enlarged scale, of part of the laser knife of FIG. 1 which surrounds an affected part.

Referring to FIGS. 1 and 2, the transmission member 3 comprises optical fibres, for example, and has its free length 3b extending through a flexible tubular member 8 which is adapated to be inserted into the coeloma. The extremity 3c of the transmission member extends into a tube 9 which is adapted to surround an affected part. As shown in FIG. 2, one end 9a of the tube is fixedly connected with the distal end of the tubular member 8, and the tube 9 is generally arcuate in configuration over almost its entire length.

The extremity 3c of the transmission member 3 is situated within a base portion 9b of the tube 9, and is formed with an emitter 3d which is located within an opening 9c formed in the base portion 9b. The opening 9c is aligned with the optical axis of the transmission member 3. Another opening 9e is formed in the inside of the free end 9d of the tube 9 in opposing relationship with the opening 9c. The laser radiation receiving element 10 is disposed in the free end 9d and has its radiation receiving surface located in the opening 9e. In this manner, the emitter 3d and the radiation receiving surface of the element 10 are aligned with each other so that laser radiation P emitted from the emitter 3d is intercepted by the radiation receiving surface. The element 10 effects a photoelectric conversion of laser radiation P, and the resulting electrical signal is fed through a lead wire 11 extending through the tube 9 and the tubular member 8 to operate electromagnetic means, not shown, which is located within the laser radiation isolation unit 4.

FIG. 4 shows a flexible tube 13 of an endoscope, either direct view type or lateral view type, which is adapted to be inserted into the coeloma. The tubular member 8 and the tube 9 of the laser knife 1 are passed through the forceps channel of the flexible tube 13 so that the tube 9 is movable out of or into the distal end 13a of the flexible tube 13.

When the laser knife 1 is used to excise an affected part such as a polyp located within the coeloma, the tube 9 is extended out of the distal end 13a of the flexible tube 13 of the endoscope so as to surround a polyp 12 while observing the latter with the endoscope. The tube 9 is positioned so that the opening 9c is located opposite to a part to be cauterized such as the base portion of polyp 12. Thereafter the laser oscillator 2 may be turned on to supply laser radiation into the transmission member 3. Thereupon, laser radiation P is conveyed through the transmission member 3 and emitted from the emitter 3d to irradiate the base portion of polyp 12, which is then cauterized and excised within a reduced time. After polyp 12 is excised, laser radiation P now impinges upon the radiation receiving surface of the element 10. In response thereto, the element 10 produces an electrical signal which is fed to the electromagnetic means within the isolation unit 4 through the lead wire 11, thus operating the unit 4 to move the isolation member 6 from its solid line to its phantom line position 6A (see FIG. 3). The path Pa is then interrupted, whereby laser radiation from the oscillator 2 is blocked from admission into the transmission member 3. This ceases the irradiation to avoid the risk that normal tissues may be inadvertently irradiated with laser radiation subsequent to the excision of an affected part. In this manner, the laser knife 1 of the invention assures a safe surgical operation of an affected part.

FIG. 5 shows another embodiment of the invention. In this instance, a tube 14 which is used to surround an affected part is V-shaped in cross section, including a pair of branch tubes 14a, 14b. A pair of openings 14c, 14d are formed in the opposing inner walls of the branch tubes adjacent to their free end. The emitter 3d at the extremity 3c of the laser radiation transmission member 3 which passes through the branch tube 14a is located in the opening 14c while the radiation receiving surface of the element 10 is located within the other opening 14d. It will be noted that in this embodiment, the path along which the laser radiation travels from the emitter to the radiation receiving element is at right angles to the optical axis of the transmission member 3 while such direction has been parallel to the optical axis in the arrangement of FIGS. 1 to 4.

FIG. 6 shows another form of isolation member 6. In this instance, the isolation member 16 is to move vertically along a rectilinear path. In other respects, the arrangement of the isolation unit 4 is similar to that shown in FIG. 3.

Figure 8:
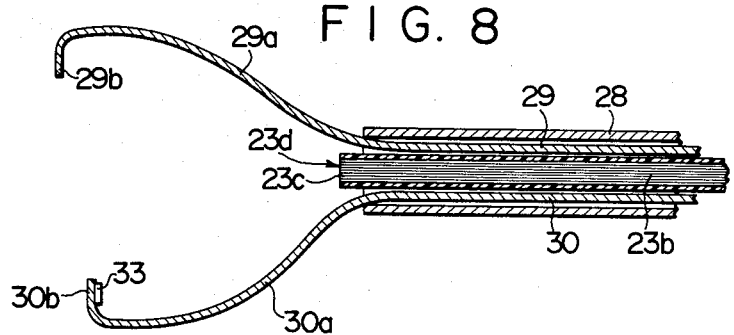
FIG. 8 is a fragmentary cross section, to an enlarged scale, of part of the laser knife of FIG. 7 which holds an affected part sandwiched between a pair of gripping arms.

FIG. 7 shows a laser knife 21 according to a further embodiment of the invention. It includes a laser oscillator 2 and laser radiation isolation unit 4, both of which are quite similar to those shown in FIGS. 3 and 6, and therefore their description will be omitted by using the same reference characters as before. The laser knife 21 includes a laser radiation transmission member 23 which may comprise a bundle of optical fibres, for example. The transmission member 23 has a free length of optical fibres 23b which, as shown in FIG. 8, is passed through a flexible tubular member 28 that is adapted to be inserted into the coeloma. The free end 23c of the transmission member is centrally located in the distal end of the tubular member 28. The free end 23c is formed with a laser radiation emitter 23d which is adapted to direct laser radiation, transmitted through the member 23, to an affected part to be cauterized for irradiation thereof.

A pair of holding members 29, 30 are received within the tubular member 28 and are freely movable therein so as to hold an affected part sandwiched therebetween. Each of the holding members 29, 30 is formed by an elongate resilient strip, and these members are disposed outside the transmission member 23 so as to be diametrically opposite to each other. The ends 29a, 30a of the members 29, 30 extend out of the distal end of the tubular member 28 and are biased apart while maintaining their opposing relationship. The extremity of each end is bent inwardly toward each other, forming a laser radiation isolator 29b and a radiation acceptor 30b. It will be noted that the end 29b is located outside the end 30b when they are in overlapping relationship (see FIG. 9). A laser radiation receiving element 33 is secured to the acceptor 30b for accepting laser radiation subsequent to the completion of the cautery of an affected part. The element 33 comprises a photoelectric transducer element which responds to laser radiation accepted by producing an electrical signal, which is fed to the electromagnetic means, not shown, located with the laser radiation isolation unit 4.

Figure 9:
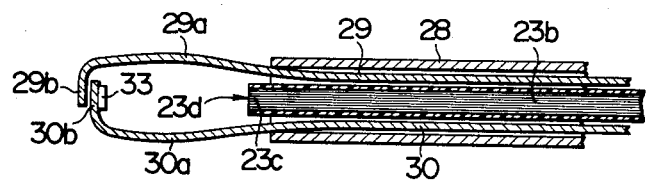
FIG. 9 is an enlarged cross section of the part shown in FIG. 8 when it is closed.

As shown in FIG. 7, the proximate ends 29c, 30c of the holding members extend out of the opposite end of the tubular member 28 and are connected with an operating member 31. The operating member 31 comprises a pair of chevron-shaped arms 31a, 31b, which are disposed back-to-back and pivotally connected together by a centrally located pin 32. The proximate ends 29c, 30c are fixedly connected with an end 31c of the arm 31a while the other arm 31b has its end which is located adjacent to the end 31c fixedly connected with the proximate end 28a of the tubular member 28. The opposite ends of the arms 31a, 31b are formed with finger receiving loops 31e, 31f. It will be understood that the operating member 31 is shaped like a scissors, but operates in the opposite manner from that of usual scissors. Specifically, when the loops 31e, 31f are moved toward each other, the ends 31c, 31d move away from each other, drawing the holding members 29, 30 into the tubular member 28 and driving the tubular member 28 in a direction toward the ends 29a, 30a of the holding members, so that the ends 29a, 30a are moved toward each other against the bias until the acceptor 30b overlaps with the isolator 29b as shown in FIG. 9. At this time, the radiation receiving surface of the element 33 is located opposite to and spaced from the emitter 23d.

Figure 10:
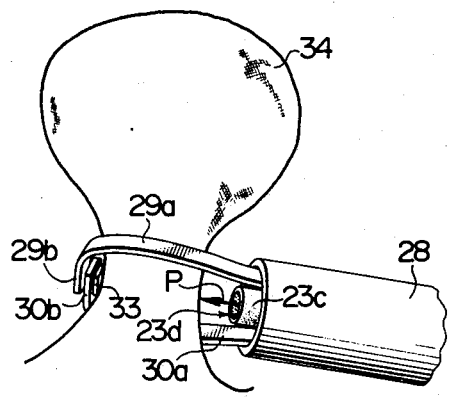
FIG. 10 is a perspective view illustrating the use of the laser knife of FIG. 7 in the excision of a polyp located within the coeloma.

When the laser knife 21 is used to cauterize the tissues of an affected part such as a polyp located with the coeloma for excision thereof, the tubular member 28 is passed through the forceps channel of an endoscope, of either direct view or lateral view type, so that the distal end of the tubular member 28, the ends 29a, 30a of the holding members and the emitter 23d can be moved out of the distal end of the endoscope. The distal end of the tubular member 28 is moved out of the endoscope and the ends 29a, 30a of the holding members positioned so as to surround a polyp while observing it with the endoscope. Subsequently, the operating member 31 is operated to hold polyp 34 sandwiched between the ends 29a, 30a as shown in FIG. 10 so that the emitter 23d is located opposite to a part to be cauterized such as the neck of polyp 34. The laser oscillator 2 is then turned on to supply laser radiation into the transmission member 23. Thereupon, laser radiation P is conveyed through the transmission member 23 and emitted from the emitter 23d toward polyp 34, thereby irradiating and cauterizing it to excise it within a reduced time. When polyp 34 is excised, laser radiation P now impinges upon the radiation receiving surface of the element 33. In response thereto, the element immediately produces an electrical signal which is fed to the electromagnetic means within the laser radiation isolation unit 4, which is thus operated to move the isolation member 6 from its solid line to its phantom line position 6A (see FIG. 3). In this manner, the path Pa along which laser radiation travels is interrupted to cease the supply of laser radiation from the oscillator 2 to the transmission member 23. This avoids the risk that normal tissues may be inadvertently irradiated with laser radiation subsequent to the excision of an affected part, thus assuring that a surgical operation upon an affected part is performed in a safe manner.

An electrical signal produced by the element 33 can be transmitted to the electromagnetic means within the isolation unit 4 by constructing the holding member 30 which carries the element 33 with an electrically conductive material and extending the proximate end 30c of the member 30 into the isolation unit 4, thus achieving the required connection with a reduced number of parts.

Figure 11:
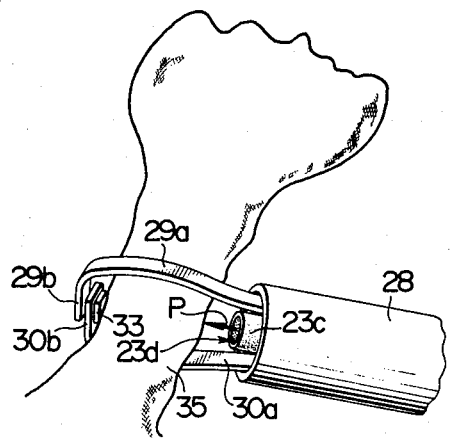
FIG. 11 is a perspective view illustrating the use of the laser knife of FIG. 7 in the cautery of a salpinx.

FIG. 11 illustrates the use of the laser knife 21 in cauterizing salpinx 35 for purpose of contraception. In this instance, the intensity of laser radiation is at a reduced level which is sufficient to cauterize salpinx 35.

Figure 12:
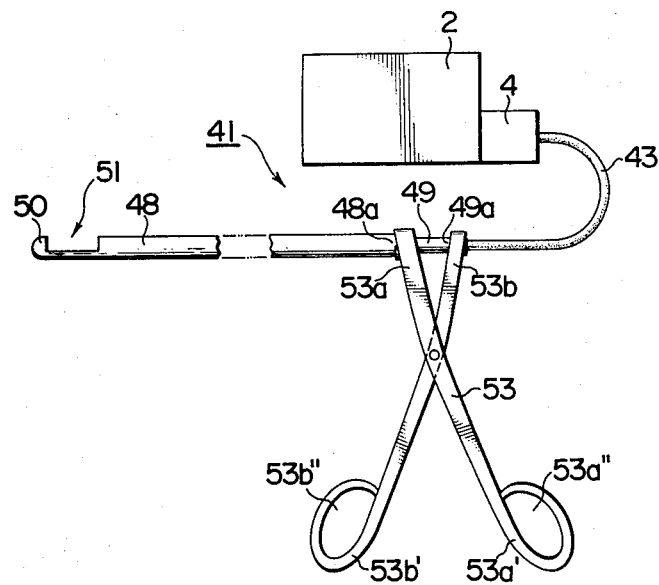
FIG. 12 is a side elevation of a laser knife according to an additional embodiment of the invention.

FIG. 12 shows a laser knife 41 according to still another embodiment of the invention. Again, the laser oscillator 2 and the laser radiation isolation unit 4 are similarly constructed as mentioned above in connection with FIGS. 3 and 6, and therefore will not be described while using the same reference characters as before.

Figure 13:
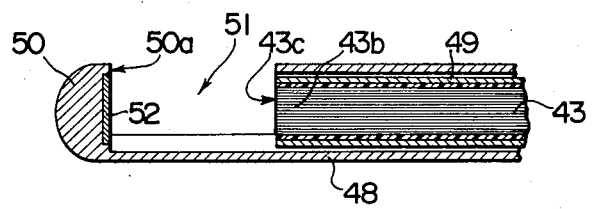
FIG. 13 is a fragmentary cross section, to an enlarged scale, of part of the laser knife of FIG. 12 which is used to hold an affected part.
Figure 14:
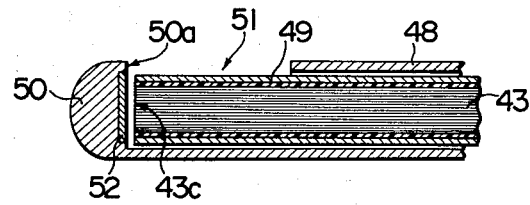
FIG. 14 is a fragmentary cross section of the part shown in FIG. 12 when it is closed.

The laser knife 41 includes a laser radiation transmission member 43, which is again formed by a bundle of optical fibres, one end of which is detachably connected with the isolation unit 4 for receiving laser radiation from the oscillator 2. The transmission member includes a free length of optical fibres 43b which is supported within a flexible, tubular retainer member 49 that is received in a flexible, tubular member 48 in a freely movable manner, as shown in FIG. 13. The free end of the transmission member is formed as an emitter 43c which directs laser radiation to an affected part for irradiation thereof. The emitter 43c forms one of holders which are used to hold an affected part therebetween. The tubular member 48 has a semi-spherical distal end 50 which defines a recess 51 for receiving an affected part, together with the emitter 43c. A radiation receiving element 52 which feeds a signal to the electromagnetic means located within the isolation unit 4 (see FIG. 3) is mounted in the inner wall 50a of the distal end 50 and is formed by a photoelectric transducer element. The radiation receiving surface of the element 52 is located in opposing relationship with the emitter 43c. The wall 50a forms the other holder. The proximate ends 48a, 49a of the tubular member 48 and retainer member 49 are fixedly connected with one end 53a, 53b, respectively, of a pair of arms which constitute a scissor-like operating member 53. The operating member 53 is formed by crossing the pair of arms and pivotally connecting them intermediate their ends. The opposite ends 53a', 53b' of the arms are formed with finger receiving loops 53a'', 53b''. When the loops are moved toward each other, the opposite ends 53a, 53b also move toward each other, whereby the tubular member 48 connected with the end 53a retracts while the retainer member 49 connected with the end 53b is drawn into the tubular member 48. In the condition shown in FIG. 12, namely, when the scissors are open, the emitter 43c at the distal end of the retainer member 49 is spaced from the distal end of the tubular member 48, as shown in FIG. 13. However, when the scissors are closed, the emitter 43c moves into abutment against the inner wall 50a of the distal end 50 of the tubular member 48, as shown in FIG. 14. If an affected part is received in the recess 51, it is held sandwiched between the emitter 43c and the inner wall 50a.

Figure 15:
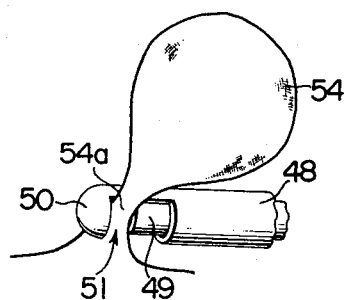
FIG. 15 is a perspective view illustrating the use of the laser knife of FIG. 12 in the excision of a polyp located within the coeloma.

When the laser knife 41 is used to excise the tissues of an affected part such as a polyp located within the coeloma, the tubular member 48 is passed through the forceps channel of an endoscope, and the tube is operated to have a part to be cauterized received within the recess 51 while observing such part with the endoscope. The operating member 53 is then closed to hold a base portion 54a of polyp 54 between the inner wall 50a and the emitter 43c, as shown in FIG. 15. The laser oscillator 2 can then be turned on to supply laser radiation into the transmission member 43. Thereupon laser radiation is emitted from the emitter 43c to irradiate the base portion 54a of the polyp, which is therefore cauterized within a reduced time to excise polyp 54.

When polyp 54 is excised, laser radiation now impinges upon the element 52 disposed in the wall 50a. The element immediately produces an electrical signal, which is fed to the electromagnetic means located within the laser radiation isolation unit 4. In response to such signal, the unit is operated to move the isolation member 6 from its solid line to its phantom line position 6A (see FIG. 3), thus interrupting the path Pa. In this manner, the risk is avoided that normal tissues may be inadvertently irradiated with laser radiation subsequent to the completion of the excision of the affected part, thus assuring a safe surgical operation of the affected part in a simple manner.

Figure 16:
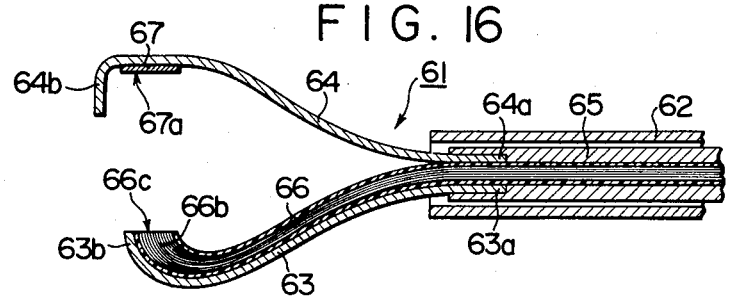
FIG. 16 is a fragmentary cross section, to an enlarged scale, of part of a laser knife according to still another embodiment of the invention.
Figure 17:
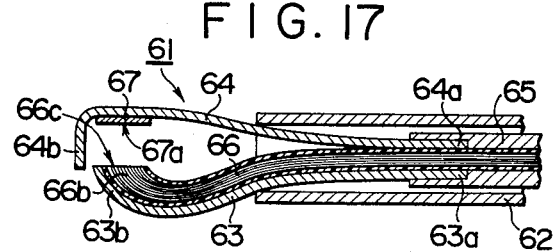
FIG. 17 is a fragmentary cross section of the part shown in FIG. 16 when it is closed.

FIGS. 16 and 17 show a laser knife 61 according to an additional embodiment of the invention. In this instance, the laser knife 61 includes a pair of holding members which can be open or closed, that is to say, moved toward or away from each other in a direction perpendicular to the length of the tubular member 48 as tubular member and retainer member are moved lengthwise thereof. Specifically, the laser knife 61 includes a tubular member 62 which internally receives a tubular retainer member 65 in a freely movable manner. A pair of holding members 63, 64 each have one end 63a, 64a fixedly connected with the retainer member 65. The holding member 63 comprises an elongate resilient strip having its distal end formed in the shape of a spoon, and its proximate end 63a connected with the retainer member 65. The other holding member 64 has its distal end 64b located generally in opposing relationship with the distal end 63b of the holding member 63 so as to overlap the latter when both members are brought together (see FIG. 17).

A laser radiation transmission member 66 extends inside the holding member 63 through the retainer member 65, and has its distal end 66b disposed on the distal end 63b of the holding member 63. The distal end 66b is located opposite to the distal end 64b of the other holding member 64 and forms an emitter 66c. A radiation receiving element 67 is disposed on a portion of the holding member 64 adjacent to the free end thereof so as to be opposite to the emitter 66c. As before, the element 67 comprises a photoelectric transducer element to supply an electrical signal to the electromagnetic menas, not shown, located within the laser radiation isolation unit (see FIG. 3).

The holding members 63, 64 extend forwardly from the distal end of the tubular member 62 and are biased apart. Both holding members can be moved toward each other until a closed position is reached as shown in FIG. 17, by axially moving either one of the tubular member 62 or retainer member 65. An affected part is adapted to be held sandwiched between the emitter 66c and the radiation receiving pad 67a, both of which serve as holders. Means for axially moving the tubular member 62 and/or retainer member 65, and the construction of the transmission member 66 in other respects are quite similar to the embodiments described previously, and therefore will not be described. It will be seen that since the holding members 63, 64 are adapted to move in a direction perpendicular to the length of the tubular member 62, an affected part of a greater volume can be held sandwiched between these holding members, thus facilitating the grasping effect.

In the embodiments described thus far, the laser radiation transmission members 3, 23, 43, 66 have been constructed by a bundle of optical fibres, but it should be understood that any other member capable of transmitting laser radiation such as glass or plastic rod, liquid fibre, or optical lenses can be used. Instead of moving the isolation members 6, 16, the laser radiation isolation unit 4 may be utilized to turn the laser oscillator on and off electrically. The tubular members 8, 28, 48, 62 used with the laser knives 1, 21, 41 and 61 of the invention may be flexible whenever the endoscope utilizes a flexible tube which is adapted to be inserted into the coeloma, or may be inflexible whenever the tube of the endoscope is inflexible.

What is claimed is:

1. A laser knife comprising a tubular member adapted to be inserted into the forceps channel of an endoscope, a laser radiation transmission member having a first end and a second end, said laser radiation transmission member being disposed within said tubular member for conveying laser radiation therethrough so that laser radiation can be conveyed from said first end of said laser radiation transmission member to be emitted from said second end of said laser radiation transmission member, means for supplying laser radiation of a power sufficient to vaporize human tissue to said first end of said transmission member, acceptor means for accepting said laser radiation emitted from said second end of said laser radiation transmission member upon completion of cautery of an affected part achieved by said laser radiation, and for producing an electrical signal in response to said laser radiation, and laser control means for terminating the transmission of said laser radiation through said laser radiation transmission member in response to said electrical signal produced by said acceptor means.

2. The laser knife of claim 1 wherein said laser control means includes laser radiation isolation means movable between a first position in the path of said laser radiation for interrupting the flow of said laser radiation into said first end of said laser radiation transmission member and a second position outside of the path of said laser radiation, said laser radiation isolation means being movable between said first and second portions in response to said electrical signal produced by said acceptor means.

3. The laser knife of claim 2 wherein said laser radiation isolation means comprises mirror means.

4. The laser knife of claim 1 wherein said acceptor means is disposed in opposing relation to said second end of said laser radiation transmission member.

5. The laser knife of claim 1 wherein said means for supplying laser radiation to said laser radiation transmission member is a laser oscillator.

6. The laser knife of claim 1 wherein said tubular member includes a non-linear end portion, said second end of said laser radiation transmission member being disposed at a first point on said non-linear end portion of said tubular member, and said acceptor means being disposed at a second point on said non-linear end portion of said tubular member.

7. The laser knife of claim 6 wherein said second point on said non-linear end portion of said tubular member is located proximate to the distal end of said tubular member and said first point on said non-linear portion of said tubular member is located distal from the distal end of said tubular member.

8. The laser knife of claim 6 wherein said non-linear end portion of said tubular member is arcuate.

9. The laser knife of claim 6 wherein said non-linear end portion of said tubular member comprises a V-shaped end portion including two ends, said second point on said non-linear end portion of said tubular member being located at one of said ends of said V-shaped portion of said tubular member and said first point on said non-linear end portion of said tubular member being located at said other end of said V-shaped portion of said tubular member.

10. The laser knife of claim 1 including retaining means axially movable within said tubular member, said retaining means including first and second holding members carried by said retaining means, said acceptor means being associated with one of said first and second holding members, said first and second holding members being biased into distal positions with respect to each other whereby said first and second holding members can operate as holders for holding said affected part therebetween when said retainer means is inserted into said tubular member.

11. The laser knife of claim 1 including retaining means carrying said laser radiation transmission member, said retaining means being axially movable within said tubular member so that the distance between said second end of said laser radiation transmission member and said acceptor means can be altered between proximate and distal positions by axially moving said retaining means, so that when said second end of said laser radiation transmission member and said acceptor means are in said proximate position with respect to each other they can operate as holders for holding an affected part therebetween.

12. The laser knife of claim 10 or 11 including displacing means for axially moving said retaining means with respect to said tubular member.

13. The laser knife of claim 12 wherein said displacing means includes a first arm affixed to said tubular member and a second arm affixed to said retaining means, said first and second arms being pivotally connected to each other.

14. The laser knife of claim 10 including a laser oscillator for supplying laser radiation to said laser radiation transmission means.

15. The laser knife of claim 10 wherein said acceptor means is associated with said first holding member and said second end of said laser radiation transmission member is associated with said second holding member.

16. The laser knife of claim 15 wherein said first and second holding members are adapted to move between said proximate and distal positions with respect to each other in a direction perpendicular to said axial direction of said tubular member.

17. The laser knife of claim 16 including displacing means for axially moving said retaining means with respect to said tubular member.

18. The laser knife of claim 17 wherein said displacing means includes a first arm affixed to said tubular member and a second arm affixed to said retaining means, said first and second arms being pivotally connected to each other.

* * * * *